US012303845B2

(12) United States Patent
Kaasalainen et al.

(10) Patent No.: US 12,303,845 B2
(45) Date of Patent: May 20, 2025

(54) METHOD FOR CRYSTALLIZATION OF ACTIVE PHARMACEUTICAL INGREDIENTS

(71) Applicant: Nanoform Finland Oyj, Helsinki (FI)

(72) Inventors: Martti Kaasalainen, Helsinki (FI); Tatiana Danilova, Helsinki (FI); Niklas Sandler, Helsinki (FI); Eric Kissi, Helsinki (FI); Nikolay Houbenov, Helsinki (FI)

(73) Assignee: Nanoform Finland Oyj, Helsinki (FI)

( * ) Notice: Subject to any disclaimer, the term of this patent is extended or adjusted under 35 U.S.C. 154(b) by 0 days.

(21) Appl. No.: 18/730,316

(22) PCT Filed: Jan. 18, 2024

(86) PCT No.: PCT/FI2024/050018
§ 371 (c)(1),
(2) Date: Jul. 19, 2024

(87) PCT Pub. No.: WO2024/191882
PCT Pub. Date: Sep. 19, 2024

(65) Prior Publication Data
US 2025/0135376 A1    May 1, 2025

(30) Foreign Application Priority Data

Jan. 18, 2023 (FI) ...................................... 20235045
May 30, 2023 (FI) ...................................... 20235606

(51) Int. Cl.
*C30B 7/00* (2006.01)
*B01D 9/00* (2006.01)
*B01D 9/02* (2006.01)

(52) U.S. Cl.
CPC .............. *B01D 9/02* (2013.01); *B01D 9/005* (2013.01); *B01D 9/0063* (2013.01); *B01D 9/0081* (2013.01); *C30B 7/00* (2013.01)

(58) Field of Classification Search
CPC .. C30B 7/00; B01D 9/02; B01D 9/005; B01D 9/0063; B01D 9/0081
See application file for complete search history.

(56) References Cited

U.S. PATENT DOCUMENTS

| 4,826,689 A | 5/1989 | Violanto et al. |
| 5,518,738 A | 5/1996 | Eickhoff et al. |

(Continued)

FOREIGN PATENT DOCUMENTS

| EP | 1347747 A2 | 10/2003 | |
| JP | 4965022 B2 * | 7/2012 | ............. A61K 38/27 |

(Continued)

OTHER PUBLICATIONS

Vaughn et al "Comparison of powder produced by evaporative precipitation into aqueous solution (EPAS) and spray freezing into liquid (SFL) technologies using novel Z-contrast STEM and complimentary techniques" European Journal of Pharmaceutics and Biopharmaceutics 60 (2005) 81-89.*

(Continued)

*Primary Examiner* — Robert M Kunemund
(74) *Attorney, Agent, or Firm* — Laine IP Oy

(57) ABSTRACT

The disclosure relates to methods for crystallization of active pharmaceutical ingredients (APIs), wherein the crystallization and crystal growth is controlled. According to the method solid amorphous nanosized API and an aqueous solution comprising one or more polymers and/or copolymers are contacted so as to form a suspension comprising nanosized API in crystalline form.

19 Claims, 8 Drawing Sheets

(56) References Cited

U.S. PATENT DOCUMENTS

| | | |
|---|---|---|
| 10,098,842 B2 | 10/2018 | Haeggström et al. |
| 2003/0096013 A1 | 5/2003 | Werling et al. |
| 2004/0028746 A1 | 2/2004 | Svenson et al. |
| 2005/0202092 A1 | 9/2005 | Skantze et al. |
| 2012/0088659 A1* | 4/2012 | Taft .................. A01N 25/10 977/700 |
| 2015/0125535 A1 | 5/2015 | Enlow et al. |

FOREIGN PATENT DOCUMENTS

| | | | |
|---|---|---|---|
| JP | 2014503446 A | | 2/2014 |
| JP | 2015520149 A | | 7/2015 |
| KR | 20170140399 A | * | 12/2017 |
| WO | WO02055059 A2 | | 7/2002 |
| WO | WO2017014314 A1 | | 1/2017 |

OTHER PUBLICATIONS

Chen et al "Transition from Amorphous Cyclosporin A Nanoparticles to SizeReduced Stable Nanocrystals in a Poloxamer 407 Solution" Molecular Pharmaceutics pp. 188-199 2022.*

Qian et al "Solution Behavior of PVP-VA and HPMC-AS-Based Amorphous Solid Dispersions and Their Bioavailability Implications" Pharm Res (2012) 29:2766-2776 DOI 10.1007/s11095-012-0695-7.*

Xia et al: Polymer-Mediated Anti-solvent Crystallization of Nitrendipine: Monodispersed Spherical Crystals and Growth Mechanism. Pharm. Res., 2012, vol. 29, pp. 158-169.

Worrall et al: Feeling the pressure: nanoparticle crystallization using controlled expansion of supercritical solution. Gordon Research Conference: Crystal engineering, 2022.

* cited by examiner

METHOD FOR CRYSTALLIZATION OF ACTIVE PHARMACEUTICAL INGREDIENTS

FIELD

The disclosure relates to methods for crystallization of active pharmaceutical ingredients (APIs), in particular to methods wherein the crystallization and crystal growth is controlled by aqueous solutions comprising one or more polymers and/or copolymers.

BACKGROUND

Many active pharmaceutical ingredients (APIs) show limited bioavailability, mainly due to their inadequate dissolution rate to treat the pathology of interest. It is well known that API dissolution rate depends on the available surface area. API particle size reduction can be used to increase the surface area and the dissolution rate. In addition, nanonization may increase solubility. Accordingly, API size reduction using micronization/nanonization techniques is a valid approach to improve the bioavailability of APIs.

It is also known that amorphous materials may have solubilities significantly higher than solubilities of the corresponding crystalline counterparts which would make amorphization an attractive option. Unfortunately, amorphous APIs tend to crystallize during processing, storage and upon administration and thus the solubility advantage may be lost. One of the most commonly used approaches to stabilize the amorphous drugs is to molecularly disperse the drug in a polymeric matrix and form an amorphous solid dispersion (ASD). However, for stabilization an ASD dose must include a significant amount of polymer.

EP1347747 discloses a method for preparing sub-micron size API comprising dissolving the API into a water-miscible first solvent to form a solution, mixing the solution into a second solvent comprising surface modifiers to produce a pre-suspension, and adding energy to the pre-suspension by homogenization, counter-current homogenization, microfluidization or sonication.

US2005202092A1 discloses methods for crystallization of API comprising rapid addition of a solution of API in organic solvent to aqueous polymeric solution.

U.S. Pat. No. 5,518,738 discloses a method for crystallization of API comprising dispersing amorphous API into a water solution of polyvinyl pyrrolidone (PVP) followed by processing through a media mill filled with polymeric milling media until the mean particle size of the API is ca 200 nm.

US20150125535A1 discloses a method for crystallizing coarse API particles by milling in aqueous Pluronic F127 until particle size is reduced to ca 270 nm.

Xia et al (Pharm. Res. 2012, 29:158-169) discloses a method for forming crystalline nitrendipine nanoparticles. In the method, nitrendipine is dissolved in a solvent of polyethylene glycol (PEG) and acetone followed by precipitation from an aqueous solution of polyvinyl alcohol, hydroxypropyl methylcellulose (HPMC) or poloxamer. The first particles that were formed were amorphous. When precipitation process continued, these particles converted to nanosized crystals provided that the process is performed at low temperature.

However, there is still need for further methods for preparation of active pharmaceutical ingredients of improved bioavailability.

SUMMARY

The present disclosure is based on the observation that when amorphous nanosized active pharmaceutical ingredients (APIs) were contacted with aqueous solutions comprising one or more polymers and/or copolymers, suspensions comprising nanosized APIs in crystalline form were obtained.

Accordingly, it is an object of the present disclosure to provide a new method for crystallization of active pharmaceutical ingredient (API), the method comprising
    providing amorphous nanosized API,
    providing an aqueous solution comprising one or more polymers and/or copolymers, and
    contacting the amorphous nanosized API and the aqueous solution comprising the one or more polymers and/or copolymers to form an admixture so as content of the amorphous nanosized API in the admixture is higher than the solubility of the amorphous nanosized API in the aqueous solution comprising the one or more polymers and/or copolymers thereby obtaining a suspension comprising the nanosized API in crystalline form.

Further aspects of the present disclosure are described in the accompanying dependent claims.

Exemplifying and non-limiting embodiments of the invention, both as to constructions and to methods of operation, together with additional objects and advantages thereof, are best understood from the following description of specific exemplifying embodiments when read in connection with the accompanying figures.

The verbs "to comprise" and "to include" are used in this document as open limitations that neither exclude nor require the existence of unrecited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION

Figure 1:
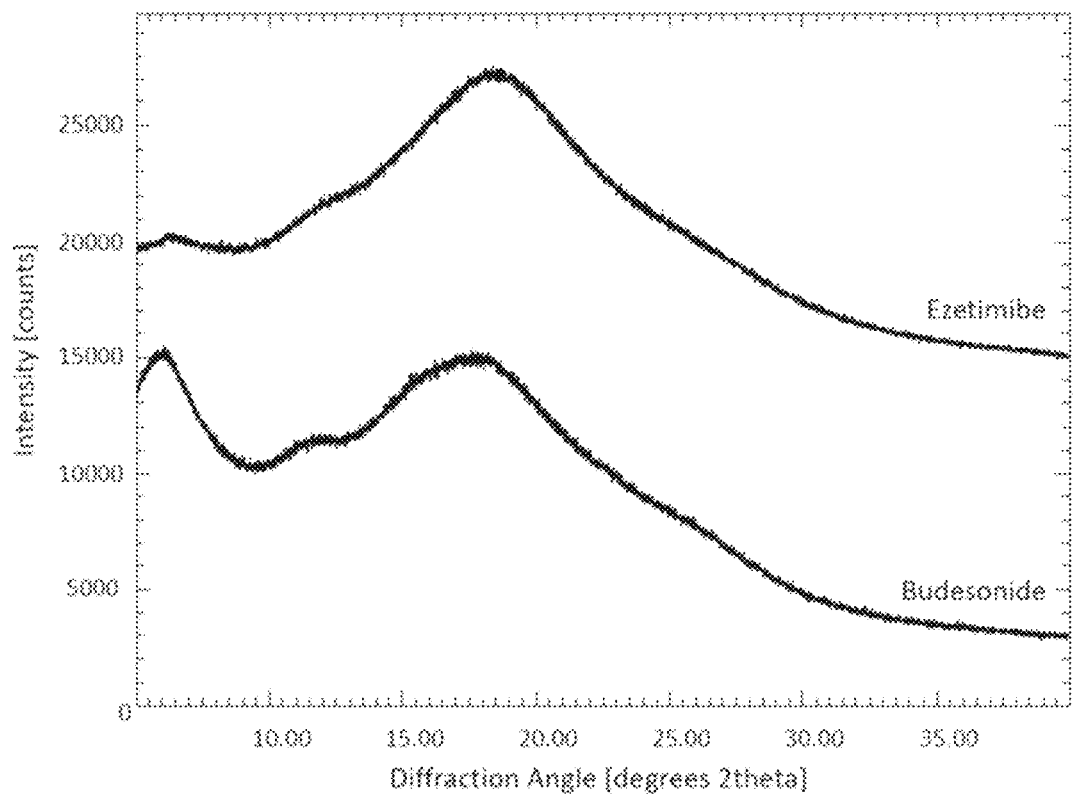
FIG. 1 shows XRD diffractogram of nanosized amorphous ezetimibe and nanosized amorphous budesonide.

As defined herein a nanosized API consists of particles which Dv90 is equal to or is less than 1000 nm, i.e., a nanosized API consist of particles which 90% of volume fraction has a diameter below 1000 nm. The API particle size may be between 10 nm and 1000 nm, for example between 10 nm and 200 nm, between 200 nm and 500 nm, or between 500 nm and 1000 nm. The size distribution can be tuned as desired since the preferred size of the nanoparticles may be API and application dependent.

As defined herein a suspension is a mixture of solids (here the API) suspended in liquid (here the aqueous solution comprising one or more polymers and/or copolymers).

As defined herein, an aqueous solution is water that contains one or more dissolved substances. The dissolved substances in an aqueous solution may be solids, or gases or other liquids.

Unless expressly stated otherwise, the term "active pharmaceutical ingredient, API" refers to the API, its non-salt form, its physiologically acceptable salts, co-crystals, polymorphs and/or solvates thereof.

According to one aspect the present disclosure concerns a method for crystallization of amorphous nanosized active pharmaceutical ingredient (API). The method comprises the following steps:
  a) providing solid amorphous nanosized API, preferably as dry powder;
  b) providing an aqueous solution comprising one or more polymers and/or copolymers; and
  c) contacting the solid amorphous nanosized API and the aqueous solution comprising the one or more polymers and/or copolymers to form an admixture so as content of the amorphous nanosized API in the admixture is higher than solubility of the amorphous nanosized API in the aqueous solution comprising the one or more polymers and/or copolymers
  thereby obtaining a suspension comprising the nanosized API in crystalline form.

Particle size growth of the API is inhibited during crystallization, and the resulting particles remain nanoparticles. For example, if the average particle size of an amorphous API is ca. 40 nm average particle size of the API crystallized using the method of the present disclosure may be ca. 120 nm. Accordingly, although the particle size of the crystalline API might be larger than particle size of amorphous API, the crystalline APIs of the present disclosure are still nanosized and the particle size does not typically grow more than 300% preferably not more than 100%, even more preferably not more than 50%, still even more preferably not more than 25%, most preferably not more than 10% upon crystallization.

The content of the amorphous nanosized API in the admixture must be higher, such as at least 10 times higher, preferably at least 50 times, more preferably at least 100 times higher, even more preferably at least 500 times higher than its solubility in the aqueous solution comprising the one or more polymers and/or copolymers to form a suspension. Accordingly, the amount of the amorphous API needed for the method is dependent on its solubility. The solubility can be measured by any method known in the art.

Typically, the contacting is at 15-40° C., preferably at 20-40° C., such as at 30° C.

According to a preferable embodiment the contacting comprises mixing the suspension. The mixing is performed preferably at least for 10 h, more preferably at least for 16 h still more preferably at least for 24 h. Relatively long mixing time is preferable to achieve complete wetting and good dispersion. The mixing can be done e.g. by shaking, stirring, or using a spatula. The mixing and wetting can be facilitated by ultrasonication. However, high-intensity ultrasound is not needed. The intensity of the ultrasound is preferably 3 W/cm$^2$ or less.

If the mixing is omitted, the contacting is performed preferably at least for 24 h.

API:polymer and/or copolymer ratio is typically from 10:1 to 1:10, more preferably from 5:1 to 1:5, most preferably from 5:1 to 1:1, such as 4:1, 3:1, 2:1 or 1:1 wherein amount of API is calculated as mg/ml of the suspension and amount of polymer and/or copolymer is calculated as weight-% of the suspension. For example, 25 mg/ml of amorphous nanosized ezetimibe with 1:1 API:polymer and/or copolymer ratio produces desired crystals in 24 h at 20° C. The optimal API:polymer ratio is dependent on the polymer and the API.

The one or more polymers and/or copolymers can be synthetic polymers or biopolymers. Exemplary polymers and copolymers suitable for the method are polyvinylpyrrolidone/vinyl acetate (PVPVA), polyvinyl acetate (PVA), polyvinyl pyrrolidone (PVP), hydroxypropyl methyl cellulose (HPMC), hypromellose acetate succinate (HPMCAS), polyacrylic acid (PAA), polyethylene glycol (PEG), polyvinyl caprolactam (PVCL), poloxamers, poly(N-vinyl caprolactam)-poly(vinyl acetate)-poly(ethylene glycol) (Soluplus®), and any co-polymer of these. Also, proteins such as wheat proteins can be used.

Too high polymer content may lead to slow crystal formation. The optimal polymer content is dependent on the polymer.

A preferable copolymer is PVPVA. Content of PVPVA in the aqueous solution is typically 0.2-50% by weight, such as 0.2-40% by weight, preferably from 10 wt.-% to 45 wt.-%.

Another preferable polymer is HPMC. Content of the HPMC in the aqueous solution is typically 0.2-5% by weight.

Still another preferable polymer is poloxamer. Content of the poloxamer in the aqueous solution is typically 0.2-40% by weight, preferably 1-20% by weight. The poloxamer is preferably selected from the group consisting of Poloxamer 331, Poloxamer 338, Poloxamer 181 Poloxamer 407, Poloxamer 182, Poloxamer 184, Poloxamer 237, Poloxamer 188, poloxamer 124, more preferably Poloxamer 407.

Preferably, the one or more polymers and/or copolymers have sufficient hydrophilicity and sufficient lipophilicity to interact with the API.

According to one embodiment, the one or more polymers and/or copolymers comprise or essentially consist of a copolymer that is derived from a first monomer and a second monomer, wherein the first monomer is more hydrophilic than the second monomer. Preferably, the first monomer in its neat state has a dipole moment that is relatively at least 0.1 Debye, preferably at least 0.2 Debye, more preferably at least 0.3 Debye, still more preferably at least 0.4 Debye greater than the dipole moment of the second monomer in its neat state.

The APIs suitable for the method are typically selected from APIs of BSC Class II and APIs of BSC Class IV.

Exemplary APIs suitable for the present disclosure are selected from the group consisting of adefovir dipivoxil, apalutamide, atazanavir, avacopan, deucravacitinib, doravirine, enzalutamide, elagolix, encorafenib, etravirine, everolimus, etonogestrel, fenofibrate, glecaprevir, pibrentasvir, grazoprevir, pibrentasvir, griseofulvin, telmisartan, itraconazole, ivacaftor, lumacaftor, tezacaftor, elexacaftor, lonafarnib, nabilone, olaparib, paclitaxel, posaconazole, pralsetinib, regorafenib, ripretinib, ritonavir, lopinavir, paritaprevir, ombitasvir, sofosbuvir, ledipasvir, suvorexant, tacrolimus, tadalafil, telaprevir, tolvaptan, vemurafenib, venetoclax, verapamil, and any combinations thereof.

By choosing appropriate conditions, crystallization can be controlled, and undesirable growth of the crystalline nanoparticles is prevented. Thus, the size of the amorphous API nanoparticles is not significantly increased by inducing crystallization under appropriate conditions.

According to one embodiment the solution comprises one or more surfactants. Exemplary surfactants suitable for the method are sodium lauryl sulfate (SLS) Tween 80, Tween 20, dioctyl sulfosuccinate sodium salt (DOSS), and tocofersolan (TPGS). The overall content of the one or more surfactants in the aqueous solution is preferably 0.0025-1.5% by weight. A particular surfactant is SLS. The surfactants enhance the wetting efficiency.

According to an exemplary embodiment the API is budesonide, and the polymer is HPMC, and the surfactant if present is SLS.

According to another exemplary embodiment the API is ezetimibe, and the copolymer is PVPVA, and the surfactant if present is SLS.

According to another exemplary embodiment the API is apalutamide, and the copolymer is PVPVA, and the surfactant if present is SLS.

According to still another exemplary embodiment the API is apalutamide, and the polymer is HPMC, and the surfactant if present SLS.

According to still another exemplary embodiment the API is ceritinib, and the polymer is poloxamer, preferably poloxamer 407, and the surfactant if present SLS.

According to one embodiment the suspension is dried to give a solid product comprising crystalline nanosized API and the one or more polymers and/or copolymers. The drying can be done by using methods known in the art. Exemplary drying methods comprise heating, evaporating, vacuum drying, using a fluidized bed dryer, spray drying, and freeze drying. A particular drying is evaporating. Crushing of the solid product using e.g. a mortar produces a powder ready for tableting. The crushing has no effect on the particle size.

The API can be isolated from wet suspension e.g., by filtering with hydrophilic filter or centrifuging and subsequently discarding the supernatant with polymer and/or copolymer solution. After this the material can be washed e.g., with water and repeating the filtering or centrifugation step. This can be repeated as many times as needed.

According to another aspect of the present disclosure concerns a process for the preparation of pharmaceutical dosage form, the process comprising
 a) granulating, preferably wet-granulating, the crystallized nanosized API obtained by the process of the present disclosure with one or more pharmaceutical excipients; and
 b) compressing the granulate.

The method of the present disclosure allows manufacture of pharmaceutical compositions and oral dosage forms containing a comparatively high dose of the API. Accordingly, tablets that can be swallowed, i.e., tablets which have a total weight of not more than about 1000 mg but still a high drug load can be produced. Also, the tablet size can be reduced since less polymer is needed than in the corresponding ASD formulations.

Materials and Methods

Bulk crystalline ezetimibe (anhydrate, CCDC*: 947148), bulk crystalline budesonide, bulk crystalline ceritinib (Form 1), and bulk crystalline apalutamide were purchased from Sinoway Industrial Co, NewChem, MSN Laboratories, and Habotech, respectively. The amorphous nanosized APIs were prepared from the bulk APIs using the process disclosed in U.S. Pat. No. 10,098,842. Permeabilities were tested using a MicroFLUX instrument (Pion Inc.). XRD diffractograms of amorphous nanosized ezetimibe and amorphous nanosized budesonide are shown in FIG. 1 as illustrative examples.

SEM images were captured using the Zeiss Sigma 300 VP SEM instruments. Samples were dispersed into water and filtered with 0.1 μm filter. Filters were dried, transferred to SEM sample holders, and coated with a 5 nm thick layer of platinum.

XRPD measurements were carried out using the Malvern PANalytical Empyrean X-ray diffractometer equipped with a Cu Kα (1.54 Å) source, MultiCore optics and a solid-state PIXcel3D detector. By using Kapton tape the samples were attached onto aluminum or polycrystalline silicon sample holders. Dried slurries were measured without further sample preparation under Kapton tape and suspensions were filtered, dried, and filters were attached with double sided tape. The samples were measured in the reflection geometry in a spinning measurement stage. The measurement range was 5-40 (°2θ). The step size and time per step values were varied depending on the counts per second obtained.

Dynamic light scattering (DLS) measurements were performed with Malvern Zetasizer. Slurries or dried powder were redispersed into water or 0.1% HPMC (aq.), stirred and measured after the sample was completely dispersed. Backscattering measurement setup was used, and CUMULANTS-algorithm was used to obtain average particle diameter (Z-average) and polydispersity index (PI).

Stability Tests

Solid material was weighted in separate vials (approx. 150 mg of material in each) and transferred to stability chambers. Three conditions were applied: ambient conditions (material in closed vial at RT), 25° C./65% RH and 40° C./75% RH. Material was analyzed at T0 as freshly prepared, T7 (7 h), T14 (14 h) and T30 (30 d) after the initiation of stability studies. SEM, XRD and dissolution/permeability studies were used to evaluate the crystallinity, particle size/morphology and performance of the material.

Dissolution Studies

The dissolution properties were measured with a Pion Rainbow R2D instrument (Pion Inc UK Ltd, Forest Row, UK). The suspensions were prepared at concentration of 5 mg/mL in 1% PVPVA suspension vehicle loaded at 40 µg/mL (ezetimibe) or 30 µg/ml (apalutamide). Fasted simulated intestinal fluid (FaSSIF) media pH 6.5 was used for dissolution studies of Ezetimibe. Dissolution studies for Apalutamide was done in biphasic mode starting in Simulated gastric media (SGF) (0.025 M HCl pH 1.6) for 15 min. Thereafter, the content of the SGF was converted to FaSSIF medium pH 6.5 by addition of 10 mL of FaSSIF concentrate media.

The temperature was set to 37° C. and stirring rate to 150 rpm. API concentrations were continuously monitored with a fiber optical UV-Vis probes path length. UV-Vis spectra were collected in 30-sec intervals using the Pion Rainbow Dynamic with either 10 mm tips for Ezetimibe or 5 mm tips for Apalutamide. The API concentration was calculated based on a standard curve using 2nd derivative data transformation (stock solution 5 mg/mL in ethanol of respective API) at a range of 293-320 nm wavelength for both Ezetimibe and Apalutamide).

Permeability Measurements (µFlux)

A µFlux instrument connected to the Rainbow instrument (Pion Inc UK Ltd, Forest Row, UK) was used to determine the passive permeability of API from different formulations. The suspensions were loaded to the donor chamber containing 10 mL of SGF (0.025 M HCl pH 1.6) and incubated for 15 min. Thereafter, the content of the donor chamber was converted to FaSSIF medium pH 6.5 by addition of 10 mL of FaSSIF concentrate media and stirring rate of 150 rpm. The receiver compartment contained 20 mL of PION acceptor buffer pH 7.4 with stirring rate of 150 rpm. The permeability was assessed across a gastrointestinal PAMPA membrane (Pion Inc UK Ltd, Forest Row, UK). The suspensions were loaded either at either 40 µg/mL for Ezetimibe or 30 µg/mL for Apalutamide using suspensions prepared at concentration of 5 mg/mL in 1 wt.-% PVPVA suspension vehicle. The temperature was set to 37° C. throughout the measurement. Incubation time was about 24 h. UV-Vis spectra were recorded at 30 s intervals at a wavelength of 293-320 nm using the Pion Rainbow Dynamic with either 10 mm tips for Ezetimibe or 5 mm tips for Apalutamide. API concentrations were calculated using second derivative to avoid interference of undissolved floating particles based on a standard curve (stock solution 5 mg/mL in ethanol). Standard curves were developed separately for SGF and FaSSIF medias for donor chamber as well as acceptor media for acceptor chamber, but the same stock solution and analysis range was used.

Determination of Crystallization

Determination of crystallization of API nanoparticles was evaluated via kinetic study of suspension. Accordingly, XRD measurement was done for suspension in different time points. Crystallization has reached its thermodynamic maximum when the peak height does not increase anymore in time.

Calculation of contents of polymers and APIs in the suspension was done as shown in table 1.

TABLE 1

| polymer (aq) % | API:polymer | Example weights | | | Final composition | | |
| --- | --- | --- | --- | --- | --- | --- | --- |
| | | polymer mg (%) | Water mg (%) | API mg | polymer wt.-% | Water wt.-% | API wt.-% |
| 15 | 1:1 | 15 | 85 | 15 | 13.0 | 73.9 | 13.0 |
| 15 | 2:1 | 15 | 85 | 30 | 11.5 | 65.4 | 23.1 |
| 20 | 1:2 | 20 | 80 | 10 | 18.2 | 72.7 | 9.1 |
| 20 | 1:1 | 20 | 80 | 20 | 16.7 | 66.7 | 16.7 |
| 20 | 2:1 | 20 | 80 | 40 | 14.3 | 57.1 | 28.6 |
| 25 | 1:2 | 25 | 75 | 12.5 | 22.2 | 66.7 | 11.1 |
| 25 | 1:1 | 25 | 75 | 25 | 20.0 | 60.0 | 20.0 |
| 1 | 2.5:1 | 1 | 99 | 2.5 | 1.0 | 96.6 | 2.4 |
| 2.5 | 1:1 | 2.5 | 97.5 | 2.5 | 2.4 | 95.1 | 2.4 |
| 5 | 1:2 | 5 | 95 | 2.5 | 4.9 | 92.7 | 2.4 |

Crystallization

Amorphous API nanoparticles (budesonide, ezetimibe, ceritinib, and apalutamide) were added as dry powders to aqueous polymer solutions. The mixtures were either (i) mixed with a magnetic stirrer and ultrasonicated until API was completely surrounded by water (wetted). The stirring was continued for 16-24 h at ambient temperature or (ii) blended with a metal spatula and allowed to stay at room temperature for 18-24 h.

The suspensions formed were analyzed after 18-24 h. SEM and XRD samples were prepared as described above. Results are presented in table 2.

Preparation of Solid Materials

Suspension comprising nanosized APIs prepared as shown above were dried in a vacuum desiccator overnight. The solid materials were grounded to produce powders. The powders were analyzed on XRD and SEM. The powders comprising nanosized APIs were used in the stability, permeability, and dissolution tests as described above. Results are presented in table 2.

TABLE 2

| | | Polymer solution | | | Suspension | | | | | Dry product | | |
|---|---|---|---|---|---|---|---|---|---|---|---|---|
| | API | Polymer | P | SLS | | | API | Excipients | Water | Total solids | API/P | LD$^f$ |
| API$^a$ | m$_{API}$$^b$ | (P) | wt.-% | wt.-% | Polymorph$^c$ | Grade$^d$ | wt-% | wt.-%* | wt.-% | wt.-% | w/w | wt.-% |
| Bude | 25 | PVPVA | 1 | | bulk | 3 | 2.4 | 1.0 | 96.6 | 3.4 | 2.5 | 71 |
| Bude | 25 | PVPVA | 2.5 | | bulk | 2 | 2.4 | 2.4 | 95.1 | 4.9 | 1.0 | 50 |
| Bude | 25 | PVPVA | 5 | | bulk | 2 | 2.4 | 4.9 | 92.7 | 7.3 | 0.5 | 33 |
| Bude | 25 | PVPVA | 1 | 0.2 | bulk | 4 | 2.4 | 1.2 | 96.4 | 3.6 | 2.1 | 68 |
| Bude | 25 | PVPVA | 2.5 | 0.2 | bulk | 4 | 2.4 | 2.6 | 94.9 | 5.1 | 0.9 | 48 |
| Bude | 25 | PVPVA | 5 | 0.2 | bulk | 4 | 2.4 | 5.1 | 92.5 | 7.5 | 0.5 | 32 |
| Bude | 25 | HPMC | 1 | | bulk | 5 | 2.4 | 1.0 | 96.6 | 3.4 | 2.5 | 71 |
| Bude | 25 | HPMC | 2.5 | | bulk | 5 | 2.4 | 2.4 | 95.1 | 4.9 | 1.0 | 50 |
| Bude | 25 | HPMC | 5 | | bulk | 5 | 2.4 | 4.9 | 92.7 | 7.3 | 0.5 | 33 |
| Bude | 25 | HPMC | 1 | 0.2 | bulk | 5 | 2.4 | 1.2 | 96.4 | 3.6 | 2.1 | 68 |
| Bude | 25 | HPMC | 2.5 | 0.2 | bulk | 5 | 2.4 | 2.6 | 94.9 | 5.1 | 0.9 | 48 |
| Bude | 25 | HPMC | 5 | 0.2 | bulk | 5 | 2.4 | 5.1 | 92.5 | 7.5 | 0.5 | 32 |
| Bude | 25 | PVP K30 | 1 | | bulk | 3 | 2.4 | 1.0 | 96.6 | 3.4 | 2.5 | 71 |
| Bude | 25 | PVP K30 | 2.5 | | bulk | 3 | 2.4 | 2.4 | 95.1 | 4.9 | 1.0 | 50 |
| Bude | 25 | PVP K30 | 5 | | bulk | 3 | 2.4 | 4.9 | 92.7 | 7.3 | 0.5 | 33 |
| Bude | 25 | Poloxamer | 1 | | bulk | 1 | 2.4 | 1.0 | 96.6 | 3.4 | 2.5 | 71 |
| Bude | 25 | Poloxamer | 2.5 | | buik | 1 | 2.4 | 2.4 | 95.1 | 4.9 | 1.0 | 50 |
| Bude | 25 | Poloxamer | 5 | | bulk | 1 | 2.4 | 4.9 | 92.7 | 7.3 | 0.5 | 33 |
| Bude | 450 | PVPVA | 45 | | bulk | 5 | 31.0 | 31.0 | 37.9 | 62.1 | 1.0 | 50 |
| Bude | 250 | PVPVA | 25 | | bulk | 5 | 20.0 | 20.0 | 60.0 | 40.0 | 1.0 | 50 |
| Bude | 200 | PVPVA | 20 | | bulk | 5 | 16.7 | 16.7 | 66.7 | 33.3 | 1.0 | 50 |
| Bude | 150 | PVPVA | 15 | | bulk | 5 | 13.0 | 13.0 | 73.9 | 26.1 | 1.0 | 50 |
| Bude | 250 | PVPVA | 25 | 0.2 | bulk | 5 | 20.0 | 20.2 | 59.8 | 40.2 | 1.0 | 50 |
| Bude | 150 | PVPVA | 15 | 0.2 | bulk | 5 | 13.0 | 13.2 | 73.7 | 26.3 | 1.0 | 50 |
| Bude | 100 | HPMC | 5 | | bulk | 5 | 9.1 | 4.5 | 86.4 | 13.6 | 2.0 | 67 |
| Bude | 150 | HPMC | 5 | | bulk | 5 | 13.8 | 4.3 | 82.6 | 17.4 | 3.0 | 75 |
| Bude | 100 | HPMC | 5 | 0.2 | bulk | 5 | 9.1 | 4.7 | 86.2 | 13.8 | 1.9 | 66 |
| Bude | 150 | HPMC | 5 | 0.2 | bulk | 5 | 13.0 | 4.5 | 82.4 | 17.6 | 2.9 | 74 |
| Eze | 25 | PVPVA | 1 | | bulk | 3 | 2.4 | 1.0 | 96.6 | 3.4 | 2.5 | 71 |
| Eze | 25 | PVPVA | 2.5 | | bulk | 2 | 2.4 | 2.4 | 95.1 | 4.9 | 1.0 | 50 |
| Eze | 25 | PVPVA | 5 | | bulk | 2 | 2.4 | 4.9 | 92.7 | 7.3 | 0.5 | 33 |
| Eze | 25 | PVPVA | 1 | 0.2 | bulk | 2 | 2.4 | 1.2 | 96.4 | 3.6 | 2.1 | 68 |
| Eze | 25 | PVPVA | 2.5 | 0.2 | bulk | 4 | 2.4 | 2.6 | 94.9 | 5.1 | 0.9 | 48 |
| Eze | 25 | PVPVA | 5 | 0.2 | hydrate | 5 | 2.4 | 5.1 | 92.5 | 7.5 | 0.5 | 32 |
| Eze | 25 | HPMC | 1 | | hydrate | 2 | 2.4 | 1.0 | 96.6 | 3.4 | 2.5 | 71 |
| Eze | 25 | HPMC | 2.5 | | hydrate | 2 | 2.4 | 2.4 | 95.1 | 4.9 | 1.0 | 50 |
| Eze | 25 | HPMC | 5 | | hydrate | 2 | 2.4 | 4.9 | 92.7 | 7.3 | 0.5 | 33 |
| Eze | 25 | HPMC | 1 | 0.2 | bulk | 2 | 2.4 | 1.2 | 96.4 | 3.6 | 2.1 | 68 |
| Eze | 25 | HPMC | 2.5 | 0.2 | amorphous | 2 | 2.4 | 2.6 | 94.9 | 5.1 | 0.9 | 48 |
| Eze | 25 | HPMC | 5 | 0.2 | amorphous | 2 | 2.4 | 5.1 | 92.5 | 7.5 | 0.5 | 32 |
| Eze | 25 | PVP K30 | 1 | | bulk | 3 | 2.4 | 1.0 | 96.6 | 3.4 | 2.5 | 71 |
| Eze | 25 | PVP K30 | 2.5 | | bulk | 3 | 2.4 | 2.4 | 95.1 | 4.9 | 1.0 | 50 |
| Eze | 25 | PVP K30 | 5 | | bulk | 3 | 2.4 | 4.9 | 92.7 | 7.3 | 0.5 | 33 |
| Eze | 25 | Poloxamer | 1 | | bulk | 1 | 2.4 | 1.0 | 96.6 | 3.4 | 2.5 | 71 |
| Eze | 25 | Poloxamer | 2.5 | | bulk | 1 | 2.4 | 2.4 | 95.1 | 4.9 | 1.0 | 50 |
| Eze | 25 | Poloxamer | 5 | | bulk | 1 | 2.4 | 4.9 | 92.7 | 7.3 | 0.5 | 33 |
| Eze | 150 | PVPVA | 15 | | hydrate | 5 | 13.0 | 13.0 | 73.9 | 26.1 | 1.0 | 50 |
| Eze | 300 | PVPVA | 15 | | hydrate | 5 | 23.1 | 11.5 | 65.4 | 34.6 | 2.0 | 67 |
| Eze | 100 | PVPVA | 20 | | hydrate | 5 | 9.1 | 18.2 | 72.7 | 27.3 | 0.5 | 33 |
| Eze | 200 | PVPVA | 20 | | hydrate | 5 | 16.7 | 16.7 | 66.7 | 33.3 | 1.0 | 50 |
| Eze | 400 | PVPVA | 20 | | hydrate | 5 | 28.6 | 14.3 | 57.1 | 42.9 | 2.0 | 67 |
| Eze | 125 | PVPVA | 25 | | hydrate | 5 | 11.1 | 22.2 | 66.7 | 33.3 | 0.5 | 33 |
| Eze | 250 | PVPVA | 25 | | hydrate | 5 | 20.0 | 20.0 | 60.0 | 40.0 | 1.0 | 50 |
| Apa | 25 | PVPVA | 1 | | new | 4 | 2.4 | 1.0 | 96.6 | 3.4 | 2.5 | 71 |
| Apa | 25 | PVPVA | 2.5 | | new | 4 | 2.4 | 2.4 | 95.1 | 4.9 | 1.0 | 50 |
| Apa | 25 | PVPVA | 5 | | new | 4 | 2.4 | 4.9 | 92.7 | 7.3 | 0.5 | 33 |
| Apa | 25 | PVPVA | 10 | | new | 4 | 2.4 | 9.8 | 87.8 | 12.2 | 0.3 | 20 |
| Apa | 25 | PVPVA | 1 | 0.2 | new | 4 | 2.4 | 1.2 | 96.4 | 3.6 | 2.1 | 68 |
| Apa | 25 | PVPVA | 2.5 | 0.2 | new | 4 | 2.4 | 2.6 | 94.9 | 5.1 | 0.9 | 48 |
| Apa | 25 | PVPVA | 5 | 0.2 | new | 4 | 2.4 | 5.1 | 92.5 | 7.5 | 0.5 | 32 |
| Apa | 25 | PVPVA | 10 | 0.2 | new | 5 | 2.4 | 10.0 | 87.6 | 12.4 | 0.2 | 20 |
| Apa | 25 | Poloxamer | 1 | | Form B | 2 | 2.4 | 1.0 | 96.6 | 3.4 | 2.5 | 71 |
| Apa | 25 | Poloxamer | 2.5 | | Form B | 2 | 2.4 | 2.4 | 95.1 | 4.9 | 1.0 | 50 |
| Apa | 25 | Poloxamer | 5 | | Form B | 2 | 2.4 | 4.9 | 92.7 | 7.3 | 0.5 | 33 |
| Apa | 25 | Poloxamer | 1 | 0.2 | Form B | 2 | 2.4 | 1.2 | 96.4 | 3.6 | 2.1 | 68 |
| Apa | 25 | Poloxamer | 2.5 | 0.2 | Form B | 2 | 2.4 | 2.6 | 94.9 | 5.1 | 0.9 | 48 |
| Apa | 25 | Poloxamer | 5 | 0.2 | Form B | 2 | 2.4 | 5.1 | 92.5 | 7.5 | 0.5 | 32 |
| Apa | 25 | HPMC | 1 | | new | 5 | 2.4 | 1.0 | 96.6 | 3.4 | 2.5 | 71 |
| Apa | 25 | HPMC | 2.5 | | new | 4 | 2.4 | 2.4 | 95.1 | 4.9 | 1.0 | 50 |
| Apa | 25 | HPMC | 1 | 0.2 | new | 5 | 2.4 | 1.2 | 96.4 | 3.6 | 2.1 | 68 |
| Apa | 25 | HPMC | 2.5 | 0.2 | new | 5 | 2.4 | 2.6 | 94.9 | 5.1 | 0.9 | 48 |
| Apa | 100 | HPMC | 5 | | amorphous | | 9.1 | 4.5 | 86.4 | 13.6 | 2.0 | 67 |
| Apa | 100 | HPMC | 5 | 0.2 | new | 5 | 9.1 | 4.7 | 86.2 | 13.8 | 1.9 | 66 |
| Apa | 150 | HPMC | 5 | 0.2 | new | 5 | 13.0 | 4.5 | 82.4 | 17.6 | 2.9 | 74 |

TABLE 2-continued

|  |  | Polymer solution | | | Suspension | | | | Dry product | | |
| --- | --- | --- | --- | --- | --- | --- | --- | --- | --- | --- | --- |
|  |  | Polymer | P | SLS |  |  | API | Excipients | Water | Total solids | API/P | LD[f] |
| API[a] | $m_{API}$[b] | (P) | wt.-% | wt.-% | Polymorph[c] | Grade[d] | wt.-% | wt.-%* | wt.-% | wt.-% | w/w | wt.-% |
| Apa | 200 | HPMC | 5 | 0.2 | new | 5 | 16.7 | 4.3 | 79.0 | 21.0 | 3.8 | 79 |
| Apa | 250 | HPMC | 5 | 0.2 | new |  | 20.0 | 4.2 | 75.8 | 24.2 | 4.8 | 83 |
| Apa | 300 | HPMC | 5 | 0.2 | new |  | 23.1 | 4.0 | 72.9 | 27.1 | 5.8 | 85 |
| Apa | 200 | PVPVA | 20 |  | new | 5 | 16.7 | 16.7 | 66.7 | 33.3 | 1.0 | 50 |
| Apa | 250 | PVPVA | 25 |  | new | 5 | 20.0 | 20.0 | 60.0 | 40.0 | 1.0 | 50 |
| Apa | 450 | PVPVA | 45 |  | new | 5 | 31.0 | 31.0 | 37.9 | 62.1 | 1.0 | 50 |
| Apa | 500 | PVPVA | 25 |  | new | 5 | 33.3 | 16.7 | 50.0 | 50.0 | 2.0 | 67 |
| Apa | 250 | PVPVA | 25 |  | new | 5 | 20.0 | 20.0 | 60.0 | 40.0 | 1.0 | 50 |
| Apa | 450 | PVPVA | 15 |  | amorphous |  | 31.0 | 10.3 | 58.6 | 41.4 | 3.0 | 75 |
| Apa | 500 | PVPVA | 25 |  | new | 5 | 33.3 | 16.7 | 50.0 | 50.0 | 2.0 | 67 |
| Apa | 600 | PVPVA | 20 |  | amorphous |  | 37.5 | 12.5 | 50.0 | 50.0 | 3.0 | 75 |
| Apa | 600 | PVPVA | 15 |  | amorphous |  | 37.5 | 9.4 | 53.1 | 46.9 | 4.0 | 80 |
| Apa | 250 | PVPVA | 25 |  | new | 5 | 20.0 | 20.0 | 60.0 | 40.0 | 1.0 | 50 |
| Apa | 450 | PVPVA | 45 | 0.2 | new | 5 | 31.0 | 31.0 | 37.9 | 62.1 | 1.0 | 50 |
| Apa | 500 | PVPVA | 25 | 0.2 | new | 5 | 33.3 | 16.7 | 50.0 | 50.0 | 2.0 | 67 |
| Apa | 150 | Poloxamer | 15 |  | Form B | 1 | 13.0 | 13.0 | 73.9 | 26.1 | 1.0 | 50 |
| Apa | 300 | Poloxamer | 15 |  | Form B | 1 | 23.1 | 11.5 | 65.4 | 34.6 | 2.0 | 67 |
| Apa | 450 | Poloxamer | 15 |  | Form B | 1 | 31.0 | 10.3 | 58.6 | 41.4 | 3.0 | 75 |
| Apa | 150 | Poloxamer | 15 | 0.2 | Form B | 1 | 13.0 | 13.2 | 73.7 | 26.3 | 1.0 | 50 |
| Apa | 300 | Poloxamer | 15 | 0.2 | Form B | 1 | 23.1 | 11.7 | 65.2 | 34.8 | 2.0 | 66 |
| Apa | 450 | Poloxamer | 15 | 0.2 | Form B | 1 | 31.0 | 10.5 | 58.5 | 41.5 | 3.0 | 75 |
| Cere | 25 | HPMC | 2.5 |  | amorphous |  | 33.3 | 16.7 | 50.0 | 50.0 | 2.0 | 67 |
| Cere | 25 | PVPVA | 2.50 |  | amorphous |  | 13.0 | 13.0 | 73.9 | 26.1 | 1.0 | 50 |
| Cere | 25 | PVPVA | 1 | 0.2 | amorphous |  | 23.1 | 11.5 | 65.4 | 34.6 | 2.0 | 67 |
| Cere | 25 | PVPVA | 2.5 | 0.2 | amorphous |  | 31.0 | 10.3 | 58.6 | 41.4 | 3.0 | 75 |
| Cere | 25 | PVPVA | 5 | 0.2 | amorphous |  | 13.0 | 13.2 | 73.7 | 26.3 | 1.0 | 50 |
| Cere | 25 | PVPVA | 10 | 0.2 | amorphous |  | 23.1 | 11.7 | 65.2 | 34.8 | 2.0 | 66 |
| Cere | 25 | Poloxamer | 1 |  | Form 1 | 5 | 31.0 | 10.5 | 58.5 | 41.5 | 3.0 | 75 |
| Cere | 25 | Poloxamer | 2.5 |  | Form 1 | 5 | 2.4 | 2.4 | 95.1 | 4.9 | 1.0 | 50 |
| Cere | 25 | Poloxamer | 5 |  | Form 1 | 5 | 2.4 | 2.4 | 95.1 | 4.9 | 1.0 | 50 |
| Cere | 25 | Poloxamer | 10 |  | Form 1 | 5 | 2.4 | 1.2 | 96.4 | 3.6 | 2.1 | 68 |
| Cere | 25 | Poloxamer | 1 | 0.2 | Form 1 | 5 | 2.4 | 2.6 | 94.9 | 5.1 | 0.9 | 48 |
| Cere | 25 | Poloxamer | 2.5 | 0.2 | Form 1 | 5 | 2.4 | 5.1 | 92.5 | 7.5 | 0.5 | 32 |
| Cere | 25 | Poloxamer | 5 | 0.2 | Form 1 | 5 | 2.4 | 10.0 | 87.6 | 12.4 | 0.2 | 20 |
| Cere | 25 | Poloxamer | 10 | 0.2 | Form 1 | 5 | 2.4 | 1.0 | 96.6 | 3.4 | 2.5 | 71 |
| Cere | 150 | Poloxamer | 15 |  | Form 1 | 5 | 2.4 | 2.4 | 95.1 | 4.9 | 1.0 | 50 |
| Cere | 300 | Poloxamer | 15 |  | Form 1 | 5 | 2.4 | 4.9 | 92.7 | 7.3 | 0.5 | 33 |
| Cere | 450 | Poloxamer | 15 |  | Form 1 | 5 | 2.4 | 9.8 | 87.8 | 12.2 | 0.3 | 20 |
| Cere | 150 | Poloxamer | 15 | 0.2 | Form 1 | 5 | 2.4 | 1.2 | 96.4 | 3.6 | 2.1 | 68 |
| Cere | 300 | Poloxamer | 15 | 0.2 | Form 1 | 5 | 2.4 | 2.6 | 94.9 | 5.1 | 0.9 | 48 |
| Cere | 150 | Poloxamer | 7.5 |  | Form 1 | 3 | 2.4 | 5.1 | 92.5 | 7.5 | 0.5 | 32 |
| Cere | 300 | Poloxamer | 7.5 |  | Form 1 | 3 | 2.4 | 10.0 | 87.6 | 12.4 | 0.2 | 20 |
| Cere | 150 | Poloxamer | 5 |  | Form 1 | 3 | 13.0 | 13.0 | 73.9 | 26.3 | 1.0 | 50 |

[a]Bude = budesonide; Eze = ezetimibe; Apa = apalutamide; Cere = ceritinib;
[b]mg of API in g of polymer solution
[c]bulk = same as the API before conversion to amorphous nanoparticles,
[d]determined from SEM figures by visual inspection 5 = nanocrystals, 1 = large crystals;
[f]loading degree.
Poloxamer was poloxamer 407.

Tableting

Formulations were manufactured by using the wet granulation technique. API loading of 20% w/w was used and tablet compression parameters (e.g., die cavity height, compression force, ejection force, strokes/min) were kept constant to investigate the impact of excipients on the tablet properties.

Figure 2:
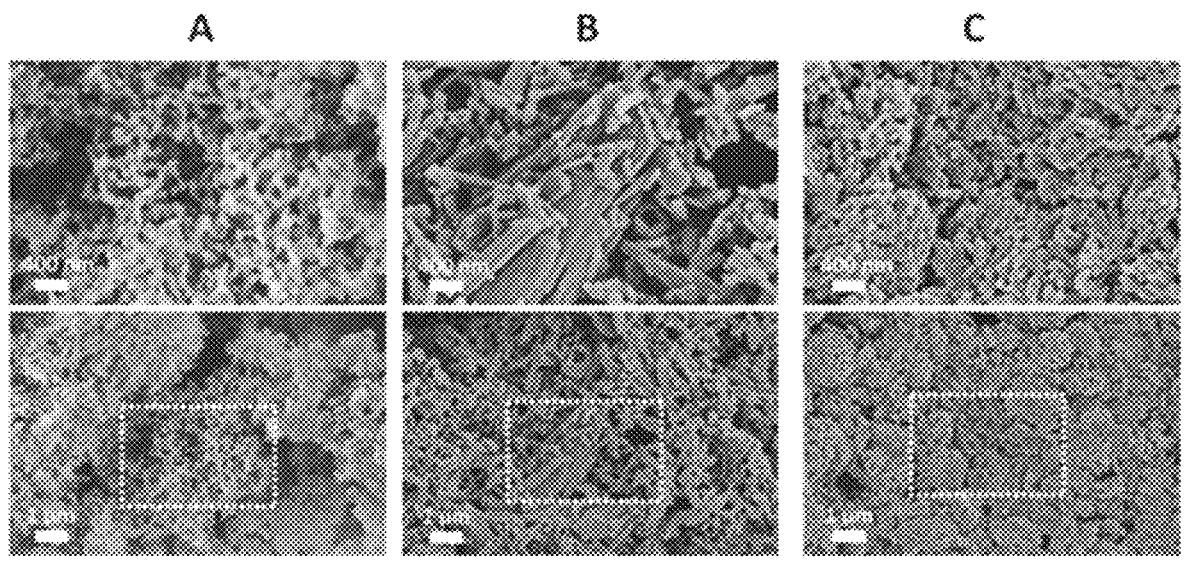
FIG. 2 shows SEM figures of A: nanosized amorphous ezetimibe, B: nanosized amorphous ezetimibe crystallized from water, and C: nanosized amorphous ezetimibe crystallized from water including 5 wt.-% PVPVA and 0.2 wt.-% SLS. The top figures are the enlargements of the areas of the corresponding bottom figures marked by dashed rectangles.

Compressed tablets can be manufactured by a process comprising the following steps:
1. Wet blending
2. Wet granulating
3. Drying
4. Grinding and sieving
5. Lubricating
6. Compressing
7. Dedusting and storing Results and Discussion FIG. 2 shows the effect of particle size and morphology on nanosized amorphous ezetimibe (A) upon crystallization from pure water (B) and from an aqueous solution comprising PVPVA (C), respectively. As seen from the figures, crystallization using the method of the present disclosure inhibits the particle size growth significantly.

Figure 3:
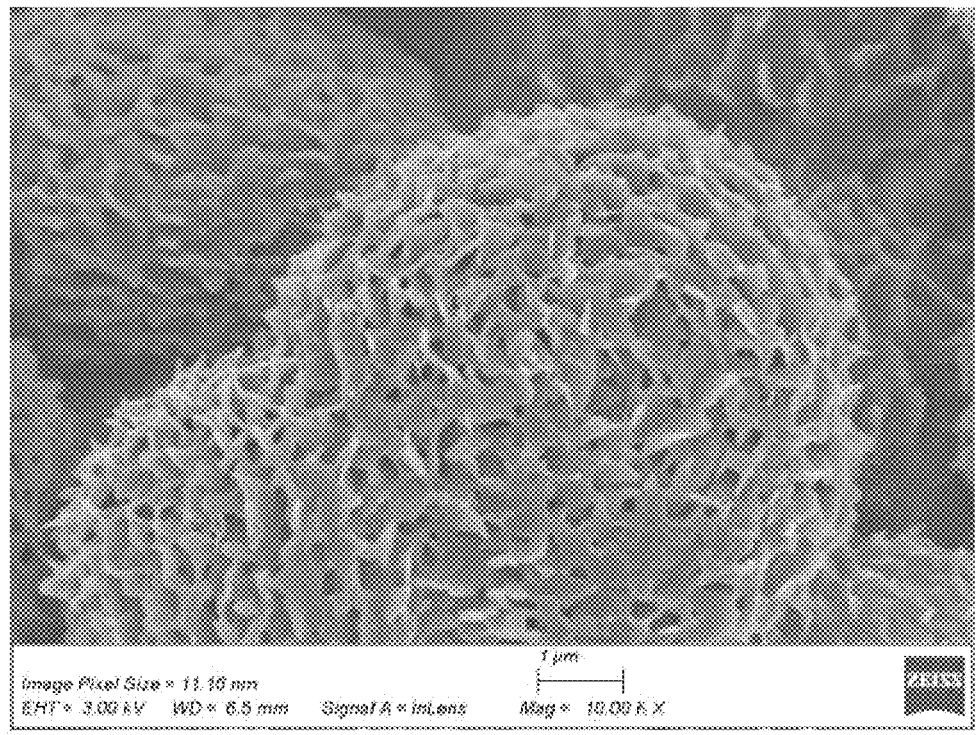
FIG. 3 shows a SEM figures of a composition comprising ceritinib nanocrystals and poloxamer 407 (dried suspension; ceritinib:poloxamer ratio 1:1; w/w). Scale bars 1 μm and 400 nm.
Figure 3:
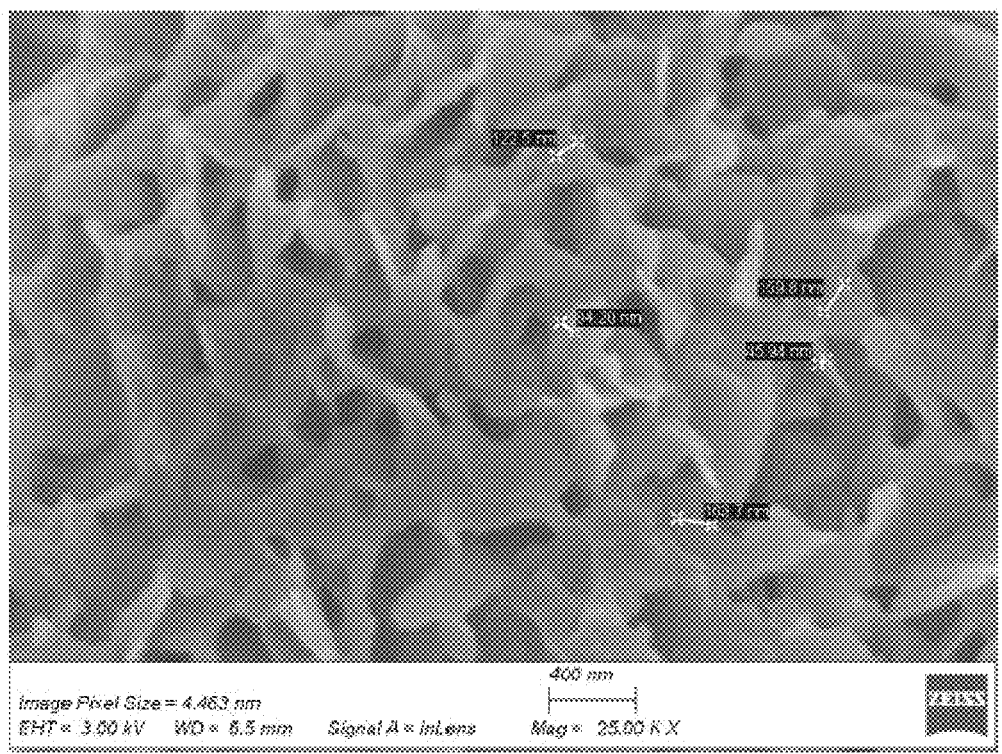

FIG. 3 shows the SEM of a composition of a dried suspensions comprising ceritinib and 15 wt.-% poloxamer 407. The API:polymer ratio was 1:1 The composition exists as uniform round-looking nanoclusters (<3 μm size) with ceritinib nanocrystals of 70-110 nm.

Figure 4:
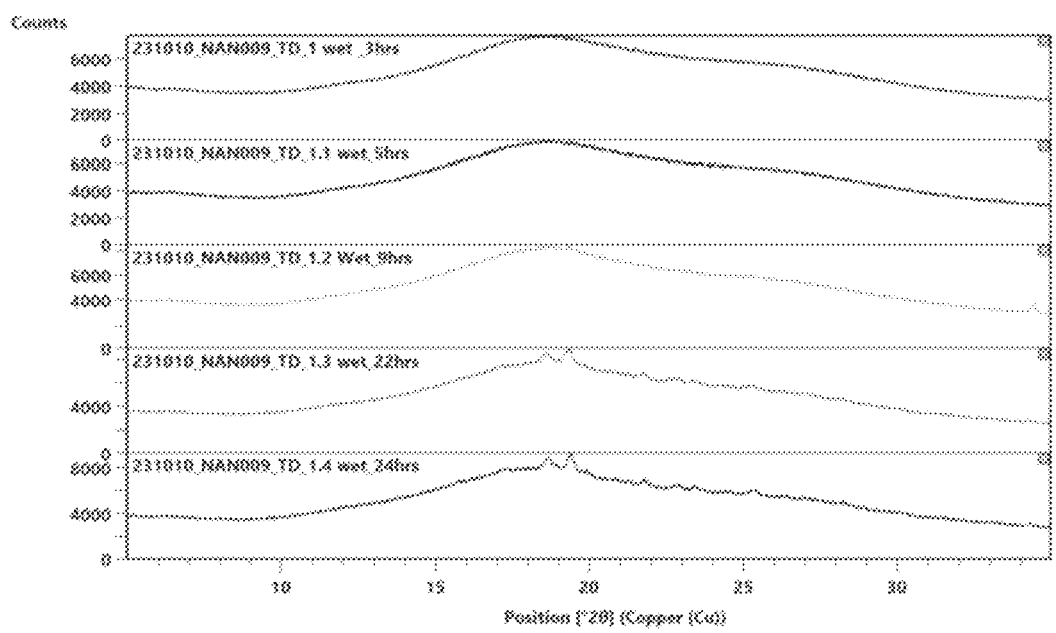
FIG. 4 shows crystallization of ezetimibe in a suspension comprising 20 wt.-% aq. PVPVA (ezetimibe:PVPVA ratio 1:1, w/w) as a function of time followed by XRD.

FIG. 4 shows XRD diffractograms of a suspension comprising ezetimibe in 20 wt.-% aq. PVPVA (API:polymer ratio 1:1) as a function of time. As seen from the figure, the crystal formation can be observed in the diffractograms only after 9 h from the contacting.

Figure 5:
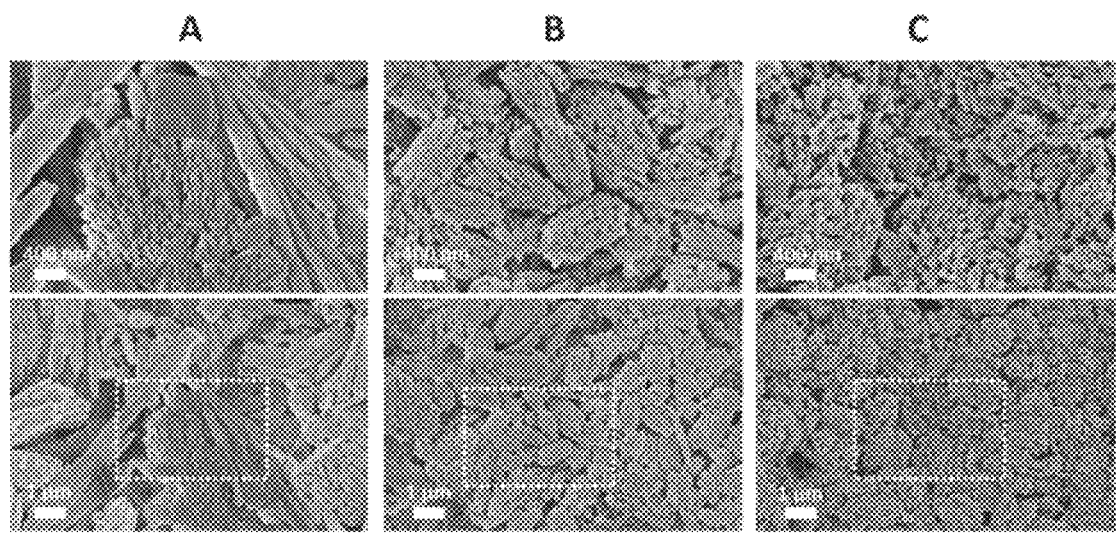
FIG. 5 shows the result of crystallization of amorphous nanosized ezetimibe as the function of PVPVA concentration. The ezetimibe concentration was 25 mg/mL, and the suspensions were mixed overnight before filtering and drying for SEM. A: 1 wt.-% PVPVA+0.2 wt.-% SLS; B: 2.5 wt.-% PVPVA+0.2 wt.-% SLS; C: 5 wt.-% PVPVA+0.2 wt.-% SLS. The top figures are the enlargements of the areas of the corresponding bottom figures marked by dashed rectangles.
Figure 6:
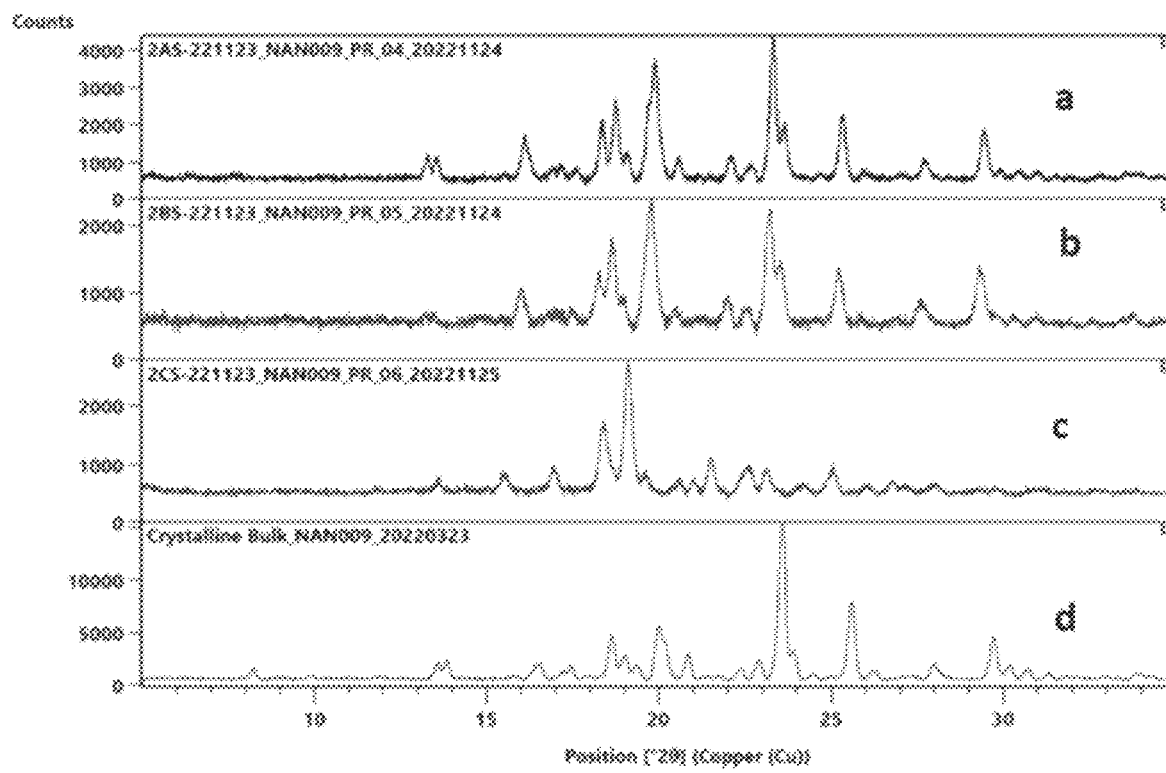
FIG. 6 shows the XRD diffractograms of ezetimibe nanocrystals (suspension of 25 mg/mL filtered and dried) of FIG. 5. a: 1 wt.-% PVPVA+0.2 wt.-% SLS; b: 2.5 wt.-% PVPVA+0.2 wt.-% SLS; c: 5 wt.-% PVPVA+0.2 wt.-% SLS; d: crystalline bulk ezetimibe.

SEM images of amorphous nanosized ezetimibe crystallized from aqueous solutions comprising three different PVPVA+SLS concentrations are shown in FIG. 5. As seen from the figure the particle size growth decreased with increasing PVPVA concentration. Crystallinity of the samples produced using an aqueous solution comprising 1 wt.-% PVPVA+0.2 wt.-% SLS (a), 2.5 wt.-%+0.2 wt.-% SLS (b) and 5 wt.-% PVPVA+0.2 wt.-% SLS (c) was characterized by XRD (FIG. 6). Crystalline bulk ezetimibe (d) is shown in the figure as a control. The results show that crystallization of amorphous nanoparticles occurred and that the crystal size control was achieved.

When PVPVA was replaced by other polymers, formation of the desired crystalline ezetimibe nanoparticles was reduced significantly. As seen from table 2, the best nanocrystals of ezetimibe were obtained when the crystallization was performed using aqueous solution comprising PVPVA, whereas the best nanocrystals of budesonide and ceritinib were produced using aqueous solution comprising HPMC, and poloxamer, respectively.

Regarding apalutamide the best nanocrystals were produced using PVPVA and HPMC. The XRD patterns of the nanocrystals indicated reflections which do not match to the polymorphic forms of apalutamide known in the patent literature up to date. This allows to conclude that the particular molecular arrangement represents a novel structural entity of nanocrystalline apalutamide, stabilized by HPMC or PVPVA.

Figure 7:
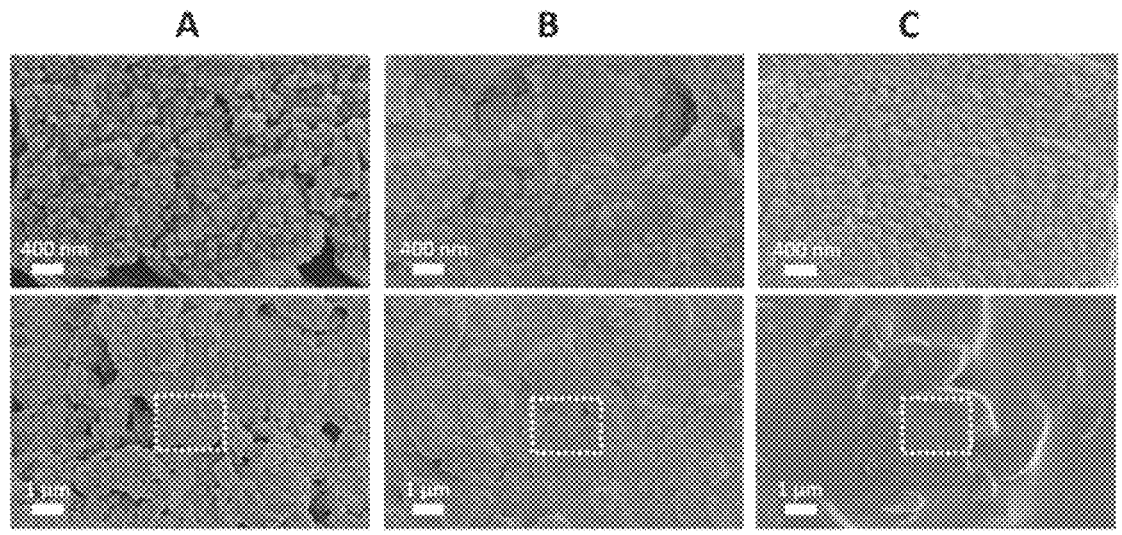
FIG. 7 shows the result of crystallization of amorphous nanosized budesonide as the function of HPMC concentration. Budesonide concentration was 25 mg/mL, and the suspensions were mixed overnight before filtering and drying for SEM. A: 1 wt.-% HPMC+0.2 wt.-% SLS; B: 2.5 wt.-% HPMC+0.2 wt.-% SLS; C: 5 wt.-% HPMC+0.2 wt.-% SLS. The top figures are the enlargements of the areas of the corresponding bottom figures marked by dashed rectangles.
Figure 8:
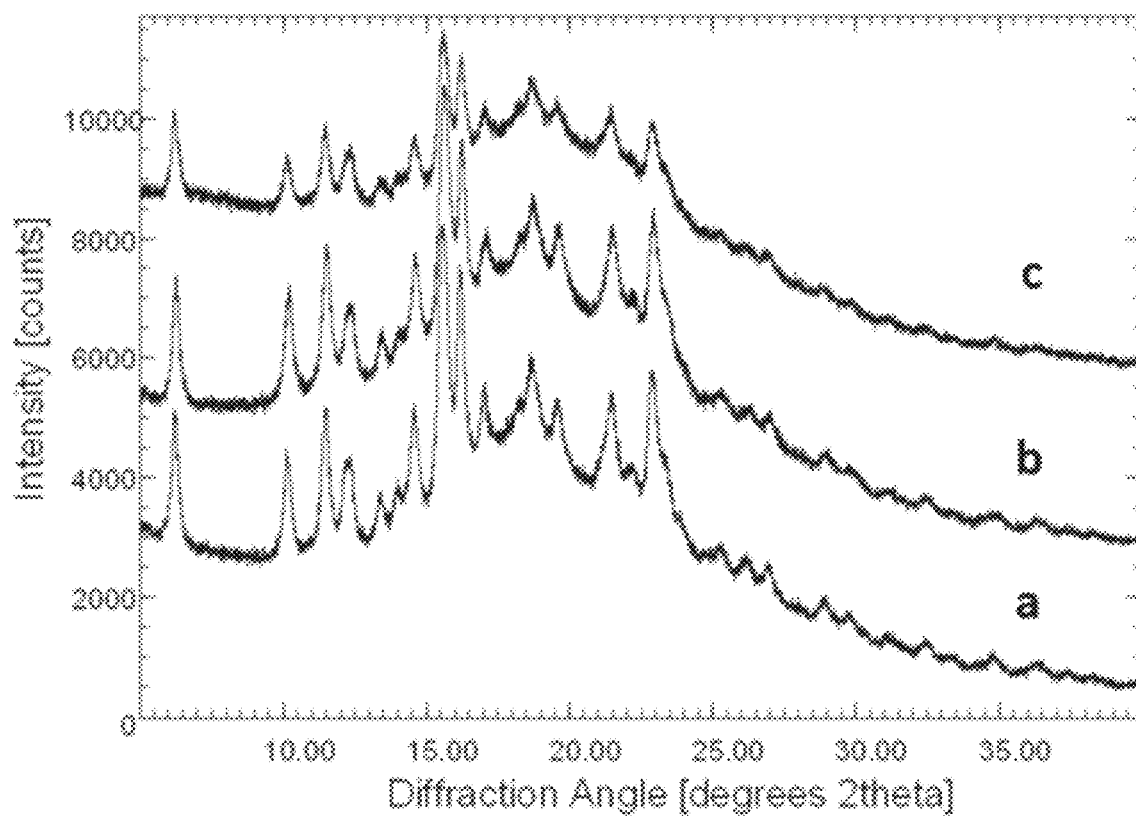
FIG. 8 shows the XRD diffractograms of budesonide nanocrystals of FIG. 7. a: 1 wt.-% HPMC+0.2 wt.-% SLS; b: 2.5 wt.-% HPMC+0.2 wt.-% SLS; c: 5 wt.-% HPMC+0.2 wt.-% SLS.

SEM images of budesonide nanoparticles crystallized from aqueous solutions comprising three different HPMC+SLS concentrations are shown in FIG. 7. Crystallinity of these samples were characterized with XRD (FIG. 8). The results show that crystallization of amorphous nanoparticles occurs, and that the particle size control was achieved with HPMC+SLS.

Crystallization of amorphous APIs can also be done in higher concentration with the limitation that also polymer concentration needs to be increased at the same time. This leads to a practical limit of 5-10 wt.-% in the case of HPMC, for example, but is a viable option with PVPVA. In fact, for PVPVA significantly higher contents such as up to 50 wt.-% can be applied.

As seen from table 2, the crystallization can be affected in particular by the polymer and ratio of the API and the polymer. Typically, addition of surfactant such as SLS assists nanocrystallization.

Figure 9:
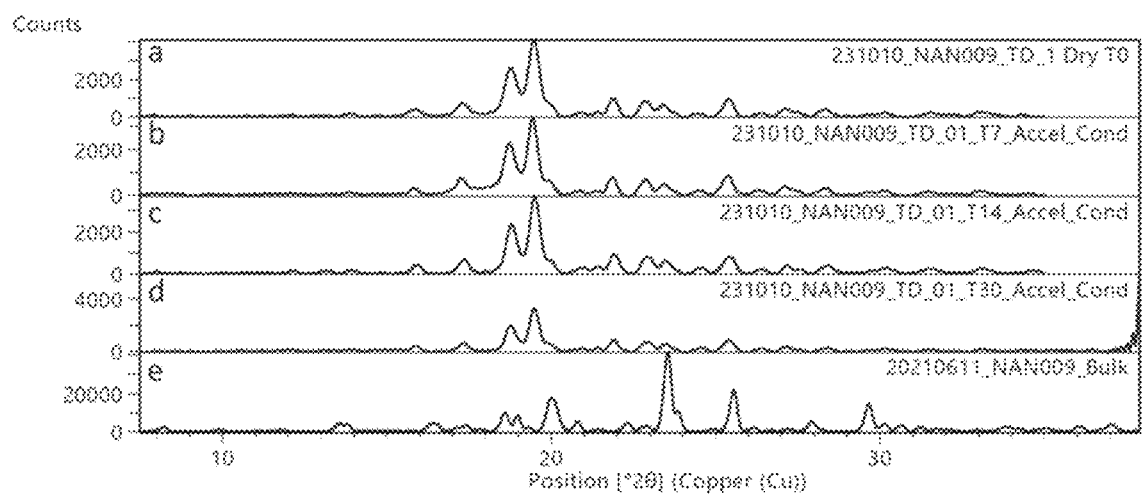
FIG. 9 shows XRD diffractograms of a dried mixture of PVPVA and nanosized crystalline ezetimibe a: just after drying; b stored for 7 h; c: stored for 14 h; d: stored for 30 d; e: bulk ezetimibe. t=40° C.; relative humidity 75%.
Figure 10:
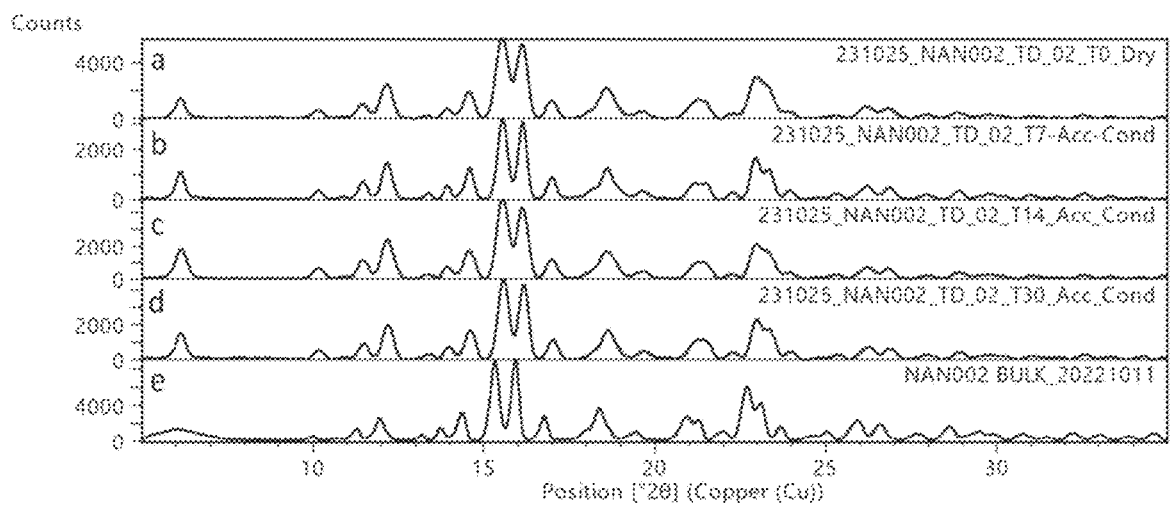
FIG. 10 shows XRD diffractograms of a dried mixture of HPMC and nanosized crystalline budesonide a: just after drying; b: stored 7 h; c: stored for 14 h; d: stored for 30 d; e: bulk budesonide. t=40° C.; relative humidity 75%.
Figure 11:
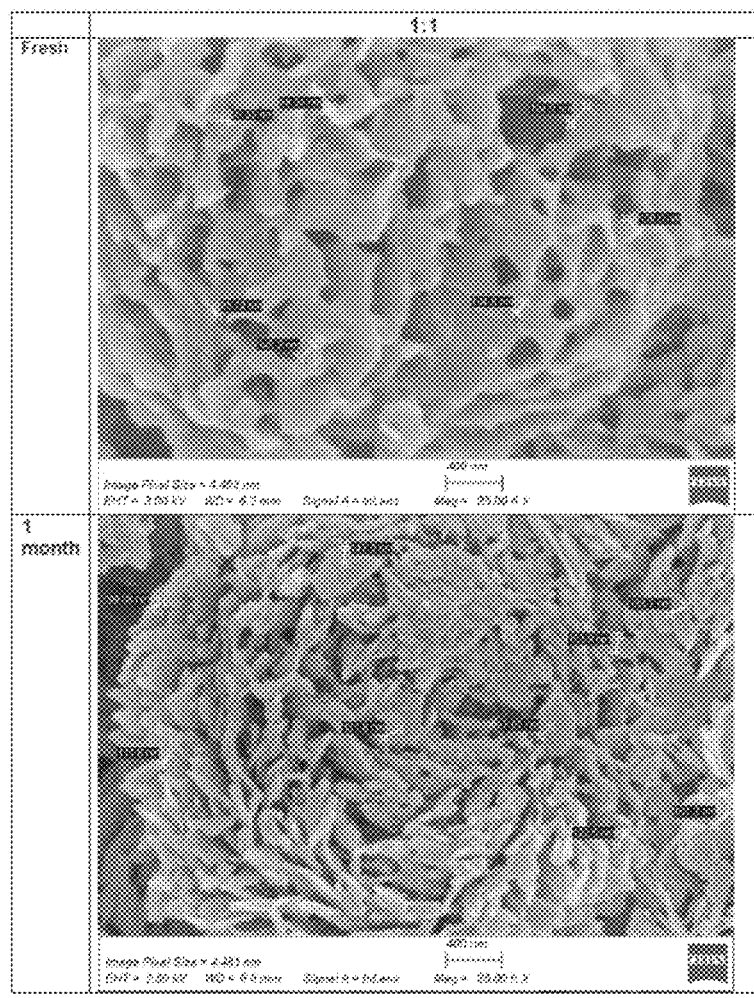
FIG. 11 shows SEM images of nanosized ceritinib composition as fresh and as stored at room temperature for one month.

Stability of nanocrystalline ezetimibe and budesonide prepared according to the present disclosure are summarized in table 3 and 4, respectively. As seen from the tables, the materials prepared were stable over the whole stability study. Crystallinities were also confirmed by XDR. XRD diffractograms of ezetimibe and budesonide stored at 40° C./75% relative humidity as a function of time is shown in FIGS. 9 and 10, respectively as illustrative examples. SEM images of ceritinib composition as fresh and as stored at room temperature for one month are shown in FIG. 11 demonstrating good stability.

TABLE 3

|  | T0 | T7 | T14 | T30 |
| --- | --- | --- | --- | --- |
| PVPVA 1:1 particle size (SEM) | 30-350 nm | 30-350 nm | 30-350 nm | 30-350 nm |
| PVPVA 1:1 HPLC | 99.77% | 99.77% 40° C./75 RH 99.77% | 99.69% 40° C./75 RH 99.68% | T0/T30 99.82% 40° C./75 RH 99.53% |

TABLE 4

|  | T0 | T7 | T14 | T30 |
| --- | --- | --- | --- | --- |
| PVPVA 1:1 particle size (SEM) | 60-400 nm | 60-400 nm | 60-400 nm | 60-400 nm |
| HPMC 3:1 particle size (SEM) | 50-300 nm | 50-300 nm | 50-300 nm | 50-300 nm |
| PVPVA 1:1 HPLC | 99.77 | T0/T7 99.79 RT 99.79 40° C./75 RH 99.75 | T0/T14 99.81 RT 99.75 40° C./75 RH 99.8 | T0/T30 99.8 RT 99.79 40° C./75 RH 99.7 |
| HPMC 3:1 HPLC | 99.77 | T0/T7 99.77 RT 99.75 40° C./75 RH 99.73 | T0/T14 99.79 RT 99.781 40° C./75 RH 99.79 | T0/T30 99.78 RT 99.74 40° C./75 RH 99.76 |

Figure 12:
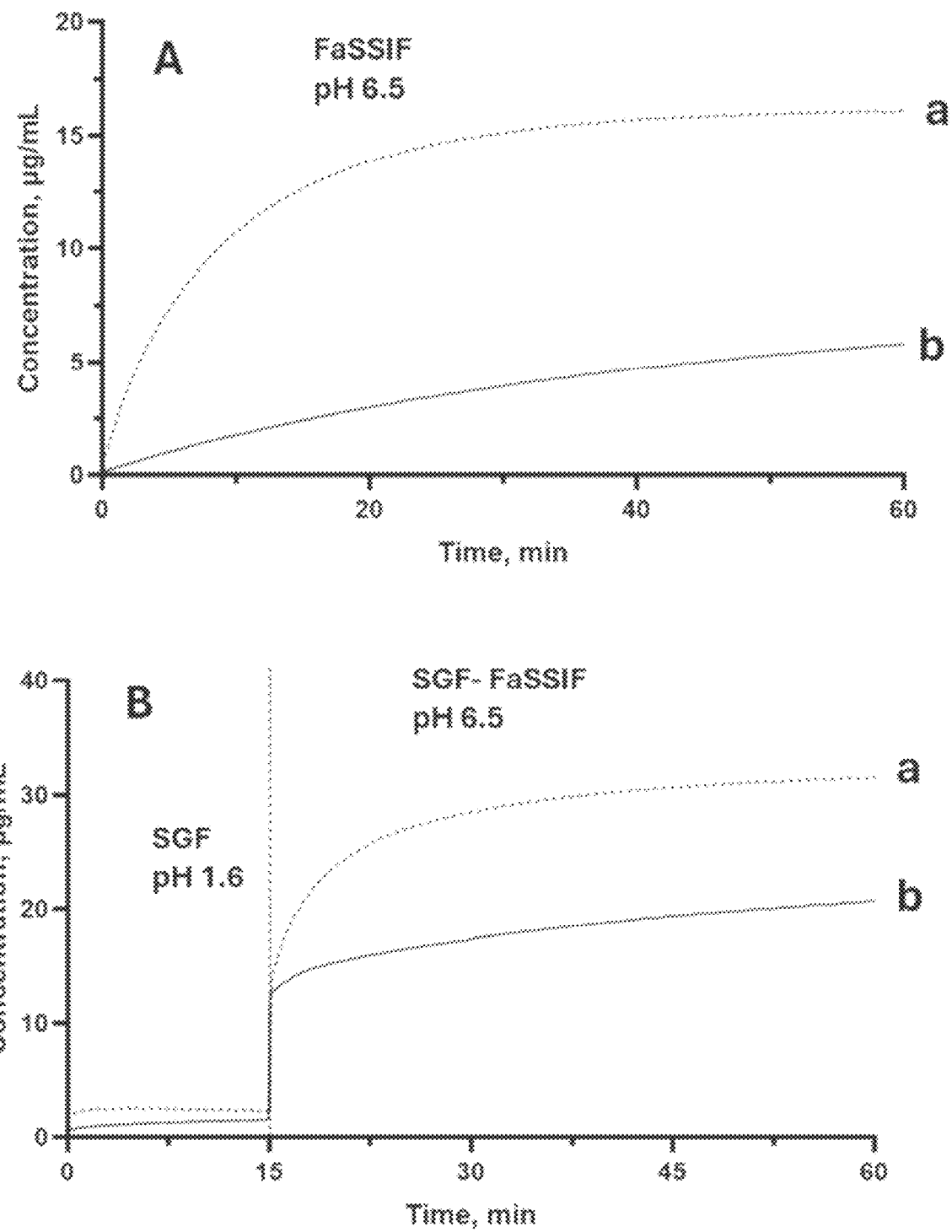
FIG. 12 shows A: FaSSIF and B: SGF-FaSSIF dissolution of a: ezetimibe prepared according to the present disclosure and b: bulk ezetimibe.

FIG. 12 shows FaSSIF and SGF-FaSSIF dissolution profiles of an exemplary ezetimibe compositions of the present disclosure and a bulk ezetimibe composition. For the experiment the compositions as powders were resuspended in aq. 1% PVPVA suspension vehicle. As clearly shown, the ezetimibe composition of the present disclosure has superior dissolution over the bulk material since it dissolves significantly faster in both fasted intestinal conditions and in fed intestinal conditions.

Figure 13:
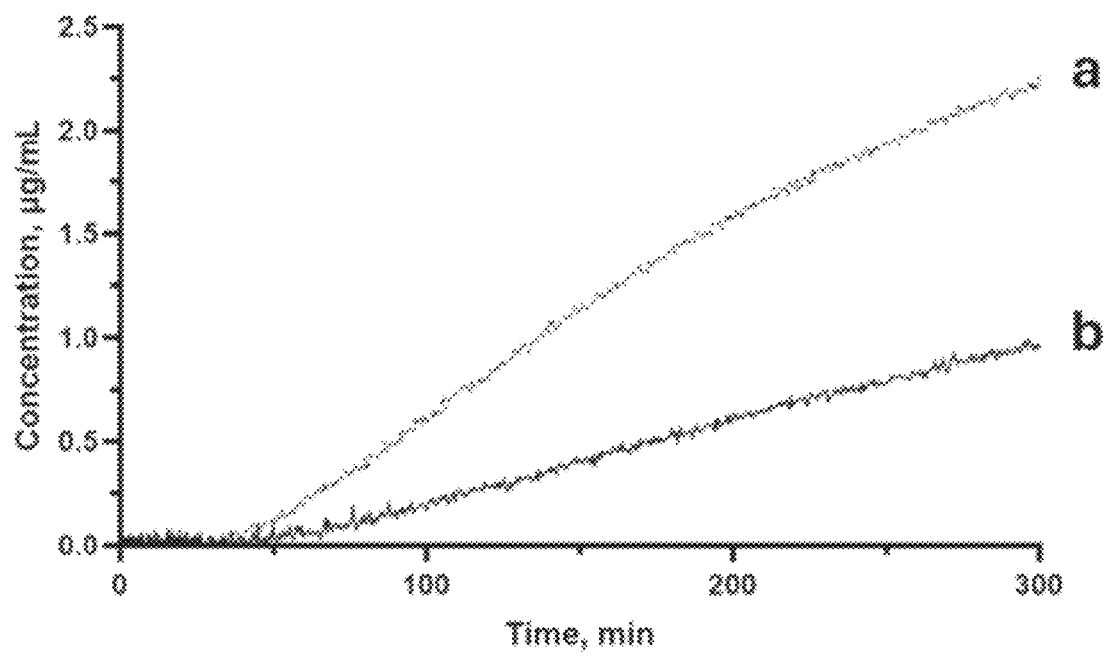
FIG. 13 shows permeabilities of a: ezetimibe prepared according to the present disclosure and b: bulk ezetimibe.

FIG. 13 shows comparison of permeability of ezetimibe compositions prepared according to the present disclosure and the corresponding bulk API. Accordingly, the permeability of the API of the present disclosure was significantly better than for the corresponding bulk API.

The advantage of the current invention in comparison to amorphous solid dispersions is that it does not require a high polymer content to stabilize the composition. Furthermore, in contrast to solvent-antisolvent methods, the method of the present disclosure it does not include the use of organic solvents which may not be completely removable by practical manufacturing techniques. Also, subjecting the API to significant mechanical force for breaking bulk API crystals into smaller ones is avoided.

What is claimed is:

1. A method for crystallization of active pharmaceutical ingredient (API), the method comprising:
   providing amorphous nanosized API;
   providing an aqueous solution comprising one or more polymers and/or copolymers; and
   contacting the amorphous nanosized API and the aqueous solution comprising the one or more polymers and/or copolymers to form an admixture wherein content of the amorphous nanosized API in the admixture is higher than solubility of the amorphous nanosized API in the aqueous solution comprising the one or more polymers and/or copolymers,
thereby obtaining a suspension comprising nanosized API in crystalline form.

2. The method according to claim 1, wherein content of the amorphous nanosized API in the admixture is at least 10 times higher than solubility of the amorphous nanosized API in the solution comprising the one or more polymers and/or copolymers.

3. The method according to claim 1, wherein API: polymer and/or copolymer ratio is from 10:1 to 1:10, wherein content of the API is calculated as mg/mL of the suspension and content of the polymer is calculated as weight-% of the one or more polymers and/or copolymers of the suspension.

4. The method according to claim 1, wherein the aqueous solution comprising one or more polymers and/or copolymers comprises one of more surfactants.

5. The method according to claim 4, wherein content of the one or more surfactants in the aqueous solution is 0.0025-1.5% by weight.

6. The method according to claim 4, wherein the one or more surfactants are selected from a group consisting of sodium lauryl sulfate (SLS) Tween 80, Tween 20, dioctyl sulfosuccinate sodium salt (DOSS), and tocofersolan (TPGS).

7. The method according to claim 1, wherein the one or more polymers are selected from a group consisting of polyvinylpyrrolidone/vinyl acetate (PVPVA), polyvinyl acetate (PVA), polyvinyl pyrrolidone (PVP), hydroxypropyl methyl cellulose (HPMC), Hypromellose acetate succinate (HPMCAS), polyacrylic acid (PAA), polyethylene glycol (PEG), polyvinyl caprolactam (PVCL), poloxamers, poly (N-vinyl caprolactam)-poly(vinyl acetate)-poly(ethylene glycol), and proteins.

8. The method according to claim 7, wherein the polymer is PVPVA, and the aqueous solution comprises 0.2-50 wt.-% PVPVA.

9. The method according to claim 7, wherein the polymer is HPMC, and the aqueous solution comprises 0.2-5 wt.-% HPMC.

10. The method according to claim 1, wherein the API is selected from APIs of BSC Class II and APIs of BSC Class IV.

11. The method according to claim 1, wherein the API is selected from the group consisting of adefovir dipivoxil, apalutamide, atazanavir, avacopan, deucravacitinib, doravirine, enzalutamide, elagolix, encorafenib, etravirine, everolimus, etonogestrel, fenofibrate, glecaprevir, pibrentasvir, grazoprevir, pibrentasvir, griseofulvin, telmisartan, itraconazole, ivacaftor, lumacaftor, tezacaftor, elexacaftor, lonafarnib, nabilone, olaparib, paclitaxel, posaconazole, pralsetinib, regorafenib, ripretinib, ritonavir, lopinavir, paritaprevir, ombitasvir, sofosbuvir, ledipasvir, suvorexant, tacrolimus, tadalafil, telaprevir, telmisartan, tolvaptan, vemurafenib, venetoclax, verapamil, and any combinations thereof.

12. The method according to claim 1, wherein the contacting comprises mixing the suspension.

13. The method according to claim 1, wherein the contacting comprises subjecting the suspension to ultrasound.

14. The method according to claim 13, wherein intensity of the ultrasound is 3 $W/cm^2$ or less.

15. The method according to claim 1, wherein the contacting is at least for 10 h.

16. The method according to claim 1, further comprising drying the suspension, thereby producing a solid comprising the nanosized API in crystalline form and the one or more polymers and/or copolymers.

17. The method according to claim 16, further comprising crushing the solid, thereby producing a powder comprising the nanosized API in crystalline form and the one or more polymers and/or copolymers.

18. The method according to claim 1, further comprising isolating the nanosized API in crystalline form from the suspension, and optionally drying the isolated nanosized API in crystalline form.

19. The method according to claim 1, wherein the particle size of the crystalline API is not more than 300% larger than the particle size of the amorphous nanosized API.

* * * * *